(12) United States Patent
Sun et al.

(10) Patent No.: US 6,835,860 B2
(45) Date of Patent: Dec. 28, 2004

(54) IODOHYDROXYLATION OF OLEFINS

(75) Inventors: Yongkui Sun, Bridgewater, NJ (US); Thorsten Rosner, North Plainfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/356,056

(22) Filed: Jan. 31, 2003

(65) Prior Publication Data

US 2003/0187291 A1 Oct. 2, 2003

Related U.S. Application Data

(60) Provisional application No. 60/353,643, filed on Feb. 1, 2002.

(51) Int. Cl.$^7$ .......................... C07C 19/07; C07C 17/02; C07C 22/02; C07C 22/04; C07C 22/08
(52) U.S. Cl. ....................... 570/244; 570/246; 570/243; 570/190; 570/216; 570/217
(58) Field of Search ................................ 570/243, 190, 570/216, 217, 244, 246, 252

(56) References Cited

U.S. PATENT DOCUMENTS

| 5,708,119 A | 1/1998 | Deisenroth et al. |
| 5,728,840 A | 3/1998 | Askin et al. |
| 5,981,759 A | 11/1999 | Sun et al. |

FOREIGN PATENT DOCUMENTS

| WO | WO 95/16658 | 6/1995 |
| WO | WO 01/38332 A1 | 5/2001 |

OTHER PUBLICATIONS

H. Ohta et al., "Iodohydrin Synthesis from Simple and Functionalised Olefins on Treatment with Periodic Acid and Sodium Bisulfite," Chemistry Letters 1990, pp. 733–736.

H. Masuda et al., "A New Synthetic Method of Preparing Iodohydrin and Bromohydrin Derivatives through in Situ Generation of Hypohalous Acids from H5IO6 and NaBrO3 in the Presence of NaHSO3," J. Org. Chem. 1994, vol. 59, pp. 5550–5555.

A. M. Sanseverino et al., "An Improved Synthesis of Beta–Iodo Ethers and Iodohydrins from Alkenes," Synthesis 1998, vol. 11, pp. 1584–1586.

A. R. De Corso et al., "Iodohydroxylation of Alkenes Promoted by Molecular and Hypervalent(III) Iodine," Tetrahedron Letters 2001, vol. 42, pp. 7245–7247.

G. Arsensio et al., "Iodomethane Oxidation by Dimethyldioxirane: A New Route to Hypoiodous Acid and Iodohydrines," Organic Letters 1999, vol. 1, No. 13, pp. 2125–2128.

K. J. Edgar et al., "An Efficient and Selective Method for the Preparation of Iodophenols," J. Org. Chem. 1990, vol. 55, pp. 5287–5291.

Y. L. Wang et al., "Kinetics of Hydrolysis of Iodine Monochloride Measured by the Pulsed–Accelerated–Flow Method," J. Am. Chem. Soc. 1989, vol. 111, pp. 7838–7844.

S. G. Yang et al., "A Practical Iodination of Aromatic Compounds Using Tetrabutylammonium Peroxydisulfate and Iodine," Tetrahedron Letters. 1999, vol. 40, pp. 6051–6054.

P.E. Maligres et al., "Diastereoselective Syn–Epoxidation of 2–Alkyl–4–Enamides to Epoxymides: Synthesis of the Merck HIV–1 Protease Inhibitor Expoxide Intermediate", Tetrahedron Letters. 1995, vol. 36, No. 13, pp. 2195–2198.

Carl R. LeBlond et al., "Harvesting Short–Lived Hypoiodous acid for efficient diastereoselective iodohydroxylation in Crixivan Synthesis", Tetrahedron Letters. 2001, vol. 42, pp. 8603–8606.

Primary Examiner—Johann R. Richter
Assistant Examiner—Elvis O. Price
(74) Attorney, Agent, or Firm—Kenneth R. Walton; Valerie J. Camara

(57) ABSTRACT

Iodohydroxylated olefins can be prepared by treating an olefin with an aqueous solution of an iodine monohalide selected from iodine monochloride and iodine monobromide.

25 Claims, No Drawings

IODOHYDROXYLATION OF OLEFINS

This application claims the benefit of U.S. Provisional Application No. 60/353,643, filed Feb. 1, 2002.

FIELD OF THE INVENTION

The present invention is directed to the iodohydroxylation of olefins using aqueous iodine monochloride or aqueous iodine monobromide.

BACKGROUND OF THE INVENTION

Iodohydrins are useful as intermediates in the preparation of pharmaceutically active compounds. For example, U.S. Pat. No. 5,728,840 and WO 01/38332 disclose iodohydrins which are useful as intermediates in the preparation of HIV protease inhibitors. Another example is WO 95/16658, which discloses the use of iodohydrins in the preparation of allylic halides that are intermediates for the synthesis of antifungal agents. Iodohydrins are also useful in the preparation of bisperfluoroalkyldiols as described in U.S. Pat. No. 5,708,119, wherein the bisperfluoroalkyldiols and their derivatives can impart oil and water repellancy to various materials such as glass, wood, paper, leather, wool, cotton and polyester.

Iodohydrins have been prepared from olefins by a variety of methods. Ohta et al., *Chem. Letters* 1990, 733–736 reports the synthesis of iodohydrins from certain alkenes, alkenols, and alkenones by treatment with periodic acid ($H_5IO_6$) and sodium bisulfite ($NaHSO_3$) under mild conditions. Masuda et al., *J. Org. Chem.* 1994, 59: 5550–5555 provides further details on the preparation of iodohydrins using $H_5IO_6+NaHSO_3$.

Sanseverino et al., *Synthesis* 1998 11: 1584–1586 discloses the preparation of β-iodo ethers and iodohydrins in relatively good yields by the reaction of alcohols and water respectively with alkenes in the presence of molecular iodine. The use of molecular iodine leads to the formation of HI during the reaction which in turn causes the reaction mixture to become increasingly acidic. This can trigger side reactions for acid sensitive reactions such as iodohydroxylation of 2-alkyl-4-enamides, as described in Maligres et al., *Tetrahedron Letters* 1995, 36: 2195. Furthermore, the presence of iodide can trigger additional side reactions as, for example, described in Sun et al, *Tetrahedron Letters* 2001, 42: 8603.

De Corso et al., *Tetrahedron Letters* 2001, 42; 7245–7247 discloses the iodohydroxylation of various olefins by treatment with a mixture of molecular iodine and phenyliodine (III)bis(trifluoroacetate) in acetonitrile-$H_2O$ solvent. The drawbacks of this approach include the use of molecular iodine (see preceding paragraph) and the expense of the trifluoroacetate oxidant. Asensio et al., *Org. Lett.* 1999, 1: 2125–2128 describes the formation of iodohydrins by the oxidation of iodomethane with dimethyldioxirane (DMDO) in acetone at −70° C., followed by addition of an olefin and slow warming of the mixture to room temperature. Unfortunately, very low temperatures are required due to the thermal instability of the reaction system. In addition, DMDO is a relatively expensive reagent.

U.S. Pat. No. 5,728,840 discloses the iodohydroxylation of an allyl acetonide by treating allyl acetonide 1 with N-iodosuccinimide (NIS) and aqueous sodium bicarbonate to provide iodohydrin 2, which is an intermediate in the preparation of indinavir, an HIV protease inhibitor:

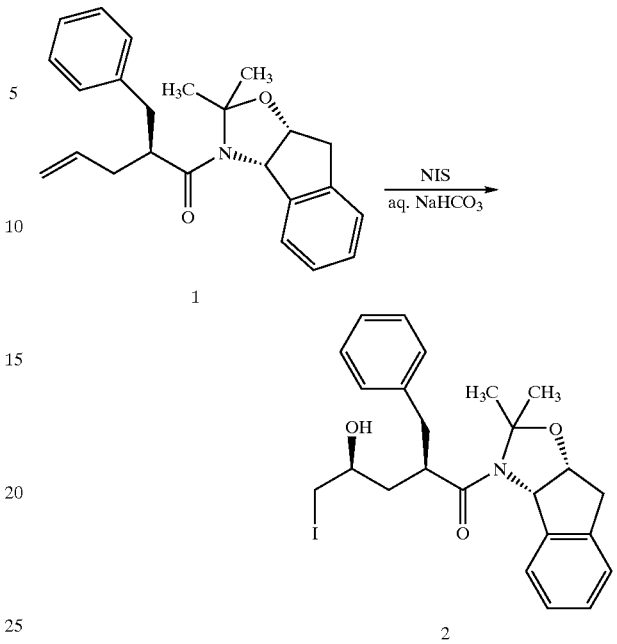

Although NIS is a practical iodohydroxylation reagent, it becomes increasingly unstable above a pH of 8 and loses its ability to iodohydroxylate due to rapid decomposition. U.S. Pat. No. 5,981,759 discloses the iodohydroxylation of allyl acetonide 1 to provide iodohydrin 2 by treating the acetonide with an aqueous solution of alkali metal hypohalite (e.g., NaOCl) and an aqueous solution of an alkali halide (e.g., NaI). While this process is characterized by high yields, operability over a wide pH range, and minimal production of organic wastes, it does exhibit a mixing sensitivity (i.e., the level of conversion decreases with increasing mixing intensity). This mixing sensitivity can present a problem during process scaleup, because mixing intensity in large vessels will vary from vessel to vessel, and can be significantly higher than that employed in typical, small-scale laboratory vessels. The process also requires two addition lines, one for the hypohalite solution and one for the halide solution, to introduce the iodohydroxylation reagent.

SUMMARY OF THE INVENTION

The present invention is an improved process for the preparation of iodohydroxylated olefins. More particularly, the present invention is a process for preparing an iodohydroxylated olefin which comprises treating an olefin with an aqueous solution of an iodine monohalide selected from iodine monochloride (ICl) and iodine monobromide (IBr). While not wishing to be bound by theory, it is believed that hypoiodous acid (HOI) is the active agent in the process of the invention and is rapidly and cleanly generated in situ via hydrolysis of ICl or IBr to provide for efficient iodohydroxylation of the olefin. The process of the invention can be operated over a relatively wide range of pH, which can be adjusted to and maintained at (i.e., "tuned" to) a value that optimizes yield of the desired iodohydroxylated product and concomitantly minimizes or suppresses by-product formation. In addition, and in contrast with the NaOCl/NaI process of U.S. Pat. No. 5,981,759 (see Background), the process of the invention is relatively insensitive to the degree of mixing/agitation of the reaction mixture; i.e., the conversion of olefin to iodohydrin exhibits little or no dependence on mixing intensity over a wide range of intensities. Further in contrast with the NaOCl/NaI process of US '759, the process of the invention utilizes only one addition line (instead of two) for the iodohydroxylation reagent, which can reduce equipment complexity and costs.

Various embodiments, aspects and features of the present invention are either further described in or will be apparent from the ensuing description, examples, and appended claims.

DETAILED DESCRIPTION OF THE INVENTION

The iodine monohalide can be iodine monochloride (ICl) or iodine monobromide (IBr). In one embodiment, the iodine monohalide is ICl.

The olefin reactant employed in the process of the invention can be any organic compound which contains at least one carbon-carbon double bond. Suitable olefin reactants include, but are not limited to, aliphatic hydrocarbon monoolefins (e.g., alkenes such as propylene, 1-butene, 2-butene, isobutene, 1-pentene, 2-pentene, 2,3-dimethyl-2-butene, and the like) and diolefins (e.g., alkadienes such as 1,3-butadiene, 1,3-pentadiene, 1,4-pentadiene, 1,4-hexadiene, and the like), alicyclic hydrocarbon olefins (e.g., cycloalkenes such as cyclopentene, cyclohexene, cycloheptene, cyclooctene, and the like) and diolefins (e.g., cycloalkadienes such as cyclopentadiene, cyclohexadiene, cyclooctadiene, and the like), mono- and di-unsaturated bicyclic hydrocarbons (e.g., norbornene, norbornadiene, 1,4-dihydronaphthalene, and indene), and alkenyl substituted aromatic hydrocarbons (e.g., styrene, α-methylstyrene, α-ethylstyrene, 1-ethenyl-2-methylbenzene, 1-ethenyl-2,6-dimethylbenzene, 1-ethenyl-2,5-dimethylbenzene, 1-phenyl-1-propylethylene, 1-phenyl-1-n-butylethylene, 1-phenyl-1-n-pentylethylene, 1-phenyl-1-n-hexylethylene, 1-phenyl-1-isopropylethylene, 1-phenyl-1-tert-butylethylene, 1-phenyl-1-cyclopropylethylene, 1-phenyl-1-cyclobutylethylene, 1-phenyl-1-cyclopentylethylene, 1-phenyl-1-cyclohexylethylene, trans-1-phenyl-2-methylethylene, cis-1-phenyl-2-methylethylene, 1-phenyl-2,2,-dimethylethylene, 1-methylene-1,2,3,4-tetrahydronaphthalene, 1-methylene-2,2-dimethyl-1,2,3,4-tetrahydronaphthalene).

Suitable olefin reactants also include, but are not limited to, unsaturated aliphatic and alicyclic halides, carboxylic acids and esters, amines, ethers, alcohols, mercaptans, aldehydes, ketones, sulfones, and alcohols. Among the suitable olefins, for example, are linear and branched alkenes and alkadienes substituted with a functional group selected from halo, hydroxy (—OH), mercapto (—SH), oxo (=O), alkoxy (—O—$C_{1-10}$ alkyl), primary amino (—$NH_2$), N-alkylamino (—NH—$C_{1-10}$ alkyl), N,N-dialkylamino (—N($C_{1-10}$ alkyl)$_2$), carboxamido (—C(=O)$NH_2$), carboxy (—COOH), alkoxycarbonyl (—C(=O)O—$C_{1-10}$ alkyl), alkylcarbonyl (—C(=O)—$C_{1-10}$ alkyl), formyl (—CHO), nitro (—$NO_2$), and cyano (—CN).

Other olefin compounds suitable for use in the present invention include, but are not limited to, acrylic esters such as the alkyl esters of acrylic acid (e.g., methyl acrylate and ethyl acrylate) and methacrylic acid (methyl methacrylate and ethyl methacrylate). Suitable olefin compounds also include cinnamic acid and esters thereof (e.g., methyl cinnamate, ethyl cinnamate, n-propyl cinnamate, isopropyl cinnamate, phenyl cinnamate, and benzyl cinnamate). Still other suitable olefin compounds include unsaturated fatty acids and fatty acid esters such as oleic acid, linoleic acid, α-linoleic acid, erucic acid, arachidonic acid, ricinoleic acid, and esters (e.g., methyl esters) thereof.

In one embodiment, the olefin reactant is an olefin is of Formula (I):

wherein each of $R^1$, $R^2$, $R^3$ and $R^4$ is independently:
(1) —H,
(2) —$CO_2R^a$,
(3) —C(=O)$R^a$,
(4) —C(=O)N($R^aR^b$),
(5) —CN,
(6) $C_{1-20}$ alkyl,
(7) $C_{2-20}$ alkenyl,
(8) $C_{3-8}$ cycloalkyl,
(9) $C_{5-8}$ cycloalkenyl,
(10) aryl, or
(11) heterocycle,
(12) $C_{1-20}$ alkyl substituted with from 1 to 3 substituents each of which is independently $C_{3-8}$ cycloalkyl, $C_{5-8}$ cycloalkenyl, aryl, or heterocycle,
(13) $C_{2-20}$ alkenyl substituted with from 1 to 3 substituents each of which is independently $C_{3-8}$ cycloalkyl, $C_{5-8}$ cycloalkenyl, aryl, or heterocycle,
(14) $C_{1-20}$ alkyl substituted with —C(=O)-aryl or —C(=O)-heterocycle, or
(15) $C_{2-20}$ alkenyl substituted with —C(=O)-aryl or —C(=O)-heterocycle;
wherein the alkyl in (6) or (12) or (14) or the alkenyl in (7) or (13) or (15) is optionally substituted with one or more substituents (e.g., from 1 to 8, or 1 to 7, or 1 to 6, or 1 to 5, or 1 to 4, or 1 to 3, or 1 or 2 substituents; or is mono-substituted) each of which is independently halogen, —OH, —CN, —O—$C_{1-6}$ alkyl, —O—$C_{1-6}$ haloalkyl, —C(=O)$R^a$, —$CO_2R^a$, —S(O)$_nR^a$, —N($R^aR^b$), —C(=O)N($R^aR^b$), N($R^a$)C(=O)—N($R^aR^b$), —C(=O)—$C_{1-6}$ alkyl-N($R^aR^b$), N($R^a$)—C(=O)—$C_{1-6}$ alkyl-N($R^aR^b$), —N($R^a$)$SO_2R^b$, or —$SO_2$N($R^aR^b$);
wherein the cycloalkyl in (8) or (12) or (13), the cycloalkenyl (9) or (12) or (13), or the aryl in (10) or (12) or (13) or (14) or (15) is optionally substituted with one or more substituents (e.g., from 1 to 6, or 1 to 5, or 1 to 4, or 1 to 3, or 1 or 2 substituents; or is mono-substituted) each of which is independently halogen, —OH, —CN, —$C_{1-6}$ alkyl, —$C_{1-6}$ haloalkyl, —O—$C_{1-6}$ alkyl, —O—$C_{1-6}$ haloalkyl, —C(=O)$R^a$, —$CO_2R^a$, —S(O)$_nR^a$, —N($R^aR^b$), —C(=O)N($R^aR^b$), —C(=O)—$C_{1-6}$ alkyl-N($R^aR^b$), phenyl, —$C_{1-6}$ alkyl-phenyl, HetA, or —$C_{1-6}$ alkyl-HetA; and
wherein the heterocycle (11) or (12) or (13) or (14) or (15) is optionally substituted with one or more substituents (e.g., from 1 to 6, or 1 to 5, or 1 to 4, or 1 to 3, or 1 or 2 substituents; or is mono-substituted) each of which is independently halogen, —OH, —CN, —$C_{1-6}$ alkyl, —$C_{1-6}$ haloalkyl, —O—$C_{1-6}$ alkyl, —O—$C_{1-6}$ haloalkyl, —C(=O)$R^a$, —$CO_2R^a$, —S(O)$_nR^a$, —N($R^aR^b$), —C(=O)N($R^aR^b$), —C(=O)—$C_{1-6}$ alkyl-N($R^aR^b$), phenyl, —$C_{1-6}$ alkyl-phenyl, —$C_{3-8}$ cycloalkyl, —$C_{1-6}$ alkyl-$C_{3-8}$ cycloalkyl, or oxo;

or alternatively $R^1$ and $R^3$ are each independently as defined above, and $R^2$ and $R^4$ together with each of the carbon atoms of the carbon-carbon double bond form $C_{5-10}$ cycloalkenyl or $C_{5-10}$ cycloalkadienyl, either of which is optionally substituted with one or more substituents (e.g., from 1 to 6, or 1 to 5, or 1 to 4, or 1 to 3, or 1 or 2 substituents; or is mono-substituted) each of which is independently halogen, $C_{1-6}$ alkyl, $C_{1-6}$ haloalkyl, —O—$C_{1-6}$ alkyl, —O—$C_{1-6}$ haloalkyl, or hydroxy;

or alternatively $R^1$ and $R^2$ are each independently as defined above, and $R^3$ and $R^4$ together with the carbon atom of the carbon-carbon double bond to which they are both attached form $C_{5-10}$ cycloalkyl or $C_{5-10}$ cycloalkenyl, either of which is optionally substituted with one or more substituents (e.g., from 1 to 6, or 1 to 5, or 1 to 4, or 1 to 3, or 1 or 2 substituents; or is mono-substituted) each of which is independently halogen, $C_{1-6}$ alkyl, $C_{1-6}$ haloalkyl, —O—$C_{1-6}$ alkyl, —O—$C_{1-6}$ haloalkyl or hydroxy;

each aryl is independently (i) an aromatic carbocyclic ring optionally substituted with 1 or 2 other aromatic carbocyclic rings or (ii) an aromatic carbocyclic fused ring system optionally substituted with 1 or 2 aromatic carbocyclic rings;

each heterocycle is independently (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; the monocyclic ring, bicyclic ring system, or tricyclic ring system contains from 1 to 6 heteroatoms independently selected from N, O and S;

each HetA is independently:

(i) a 4- to 7-membered saturated heterocyclic ring containing from 1 to 4 heteratoms selected from N, O and S, wherein the saturated heterocyclic ring is optionally substituted with from 1 to 3 substituents each of which is independently halogen, —$C_{1-4}$ alkyl, or oxo, or (ii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl;

each n is an integer independently equal to zero, 1 or 2; and each $R^a$ and $R^b$ is independently —H or —$C_{1-6}$ alkyl.

A class of suitable olefin reactants includes the olefins of Formula (I), wherein each $R^a$ and $R^b$ is independently —H or —$C_{1-4}$ alkyl; and all other variables are as originally defined. An aspect of this class includes olefins of Formula (I), wherein each $R^a$ and $R^b$ is independently a —$C_{1-4}$ alkyl group. A sub-class of the preceding class includes olefins of Formula (I), in which each $R^a$ and $R^b$ is independently —H, methyl or ethyl; and all other variables are as originally defined. An aspect of this sub-class includes olefins of Formula (I), in which each $R^a$ and $R^b$ is independently —H or methyl. Other aspects of this sub-class include olefins of Formula (I) in which each $R^a$ and $R^b$ is —H; and in which each $R^a$ and $R^b$ is methyl.

A class of suitable olefin reactants includes the aliphatic hydrocarbon mono-olefins of Formula (I), wherein each of $R^1$, $R^2$, $R^3$ and $R^4$ is independently —H or $C_{1-20}$ alkyl. A sub-class of the aliphatic hydrocarbon mono-olefins includes mono-olefins of Formula (I), in which two of $R^1$, $R^2$, $R^3$ and $R^4$ are —H, and the other two of $R^1$, $R^2$, $R^3$ and $R^4$ are each independently —H or $C_{1-20}$ alkyl. Another sub-class of the aliphatic hydrocarbon mono-olefins includes mono-olefins of Formula (I), in which $R^1$ is —H or $C_{1-20}$ alkyl, and each of $R^2$, $R^3$ and $R^4$ is —H. Another sub-class of the aliphatic hydrocarbon mono-olefins includes mono-olefins of Formula (I), in which $R^1$ is $C_{1-20}$ alkyl, and each of $R^2$, $R^3$ and $R^4$ is —H.

Another class of suitable olefin reactants includes the aliphatic hydrocarbon diolefins of Formula (I), wherein one of $R^1$, $R^2$, $R^3$ and $R^4$ is $C_{2-20}$ alkenyl, and each of the others of $R^1$, $R^2$, $R^3$ and $R^4$ is independently —H or $C_{1-20}$ alkyl. A sub-class of the aliphatic hydrocarbon diolefins includes diolefins of Formula (I), in which one of $R^1$, $R^2$, $R^3$ and $R^4$ is $C_{2-20}$ alkenyl, another of $R^1$, $R^2$, $R^3$ and $R^4$ is $C_{1-20}$ alkyl, and the remaining two of $R^1$, $R^2$, $R^3$ and $R^4$ are —H. Another sub-class of the aliphatic hydrocarbon diolefins includes diolefins of Formula (I), in which $R^1$ is $C_{2-20}$ alkenyl, and each of $R^2$, $R^3$ and $R^4$ is —H.

Another class of suitable olefin reactants includes the aryl-substituted aliphatic hydrocarbon mono-olefins of Formula (I), wherein one of $R^1$, $R^2$, $R^3$ and $R^4$ is aryl or —$C_{1-20}$ alkyl-aryl; and each of the others of $R^1$, $R^2$, $R^3$ and $R^4$ is —H or $C_{1-20}$ alkyl. A sub-class of the aryl-substituted aliphatic hydrocarbon mono-olefins includes mono-olefins of Formula (I), in which one of $R^1$ and $R^2$ is aryl or —$C_{1-10}$ alkyl-aryl; the other of $R^1$ and $R^2$ is —H; one of $R^3$ and $R^4$ is —H or $C_{1-20}$ alkyl; and the other of $R^3$ and $R^4$ is —H. Another sub-class of the aryl-substituted aliphatic hydrocarbon mono-olefins includes mono-olefins of Formula (I), wherein one of $R^1$ is aryl or —$C_{1-6}$ alkyl-aryl; $R^2$ is —H; one of $R^3$ and $R^4$ is —H or $C_{1-10}$ alkyl; and the other of $R^3$ and $R^4$ is —H.

Another class of suitable olefin reactants includes the aryl-substituted aliphatic hydrocarbon diolefins of Formula (I), wherein one of $R^1$, $R^2$, $R^3$ and $R^4$ is —$C_{2-20}$ alkenyl-aryl; and each of the others of $R^1$, $R^2$, $R^3$ and $R^4$ is —H or $C_{1-20}$ alkyl. A sub-class of the aryl-substituted aliphatic hydrocarbon diolefins includes diolefins of Formula (I), in which one of $R^1$ and $R^2$ is —$C_{2-10}$ alkenyl-aryl; the other of $R^1$ and $R^2$ is —H; one of $R^3$ and $R^4$ is —H or $C_{1-20}$ alkyl; and the other of $R^3$ and $R^4$ is —H. Another sub-class of the aryl-substituted aliphatic hydrocarbon diolefins includes diolefins of Formula (I), in which $R^1$ is —CH=CH-aryl; $R^2$ is —H; one of $R^3$ and $R^4$ is —H or $C_{1-10}$ alkyl; and the other of $R^3$ and $R^4$ is —H. Another sub-class of the aryl-substituted aliphatic hydrocarbon diolefins includes diolefins of Formula (I), in which $R^1$ is —CH=CH$_2$; $R^2$ is —H; one of $R^3$ and $R^4$ is —$C_{1-10}$ alkyl-aryl; and the other of $R^3$ and $R^4$ is —H.

Another embodiment of suitable olefin reactants includes heterocyclic-containing allyl compounds of Formula (I), wherein $R^1$, $R^2$, and $R^3$ are all —H; and $R^4$ is $C_{1-20}$ alkyl which is:

(i) optionally substituted with $C_{3-6}$ cycloalkyl, aryl, or HetB, wherein the cycloalkyl, aryl, or HetB is optionally substituted with one or more substituents (e.g., from 1 to 4, or 1 to 3, or 1 or 2 substituents; or is mono-substituted) each of which is independently halogen, —OH, —$C_{1-6}$ alkyl, —$C_{1-6}$ haloalkyl, —O—$C_{1-6}$ alkyl, or —O—$C_{1-6}$ haloalkyl;

wherein HetB is a 5- or 6-membered heteroaromatic ring containing from 1 to 4 heteroatoms independently selected from N, O and S; and (ii) substituted with —(C=O)-heterocycle, wherein the heterocycle is optionally substituted with one or more substituents (e.g., from 1 to 6, or 1 to 5, or 1 to 4, or 1 to 3, or 1 or 2 substituents; or is mono-substituted) each of which is independently halogen, —OH, —$C_{1-6}$ alkyl, —$C_{1-6}$ haloalkyl, —O—$C_{1-6}$ alkyl, or —O—$C_{1-6}$ haloalkyl.

A class of the heterocyclyl allyl reactants includes compounds of Formula (I), wherein $R^1$, $R^2$, and $R^3$ are all —H; and $R^4$ is $C_{1-10}$ alkyl which is (i) substituted with an aryl selected from the group consisting of phenyl and naphthyl and is (ii) substituted with —(C=O)-heterocycle, wherein the heterocycle is optionally substituted with from 1 to 5 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl.

Another class of the heterocyclic-containing allyl reactants includes compounds of Formula (II):

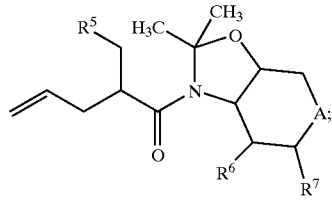

(II)

wherein A is absent, $CH_2$, O, or S;
$R^5$ is $C_1$–$C_6$ alkyl, $C_3$–$C_6$ cycloalkyl, phenyl, naphthyl, or HetB; wherein the alkyl, cycloalkyl, phenyl, naphthyl, or HetB is optionally substituted with one or more substituents (e.g., from 1 to 4, or 1 to 3, or 1 or 2 substituents; or is mono-substituted) each of which is independently halogen, hydroxy, —$C_1$–$C_6$ haloalkyl, —O—$C_1$–$C_6$ alkyl, or —O—$C_1$–$C_6$ haloalkyl;
HetB in $R^5$ is a 5- or 6-membered monocyclic aromatic ring containing from 1 to 4 heteroatoms independently selected from N, O and S; and
$R^6$ and $R^7$ are each independently —H, —$C_1$–$C_6$ alkyl, —$C_1$–$C_6$ haloalkyl, —$C_3$–$C_6$ cycloalkyl, or aryl, wherein aryl is selected from phenyl and naphthyl, and is optionally substituted with one or more substituents (e.g., from 1 to 4, or 1 to 3, or 1 or 2 substituents; or is mono-substituted) each of which is independently halogen, —OH, —$C_1$–$C_6$ alkyl, —$C_1$–$C_6$ haloalkyl, —O—$C_1$–$C_6$ alkyl, or —O—$C_1$–$C_6$ haloalkyl; or alternatively
$R^6$ and $R^7$ together with the carbons to which each is attached form a fused benzene ring which is optionally substituted with one or more substituents (e.g., from 1 to 4, or 1 to 3, or 1 or 2 substituents; or is mono-substituted) each of which is independently halogen, —OH, —$C_1$–$C_6$ alkyl, —$C_1$–$C_6$ haloalkyl, —O—$C_1$–$C_6$ alky, or —O—$C_1$–$C_6$ haloalkyl.

Another class of the heterocyclic-containing allyl reactants includes compounds of Formula (III), (IV), (V), and (VI):

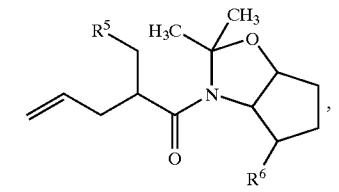

(III)

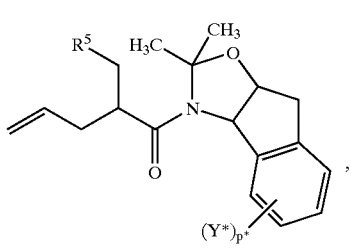

(IV)

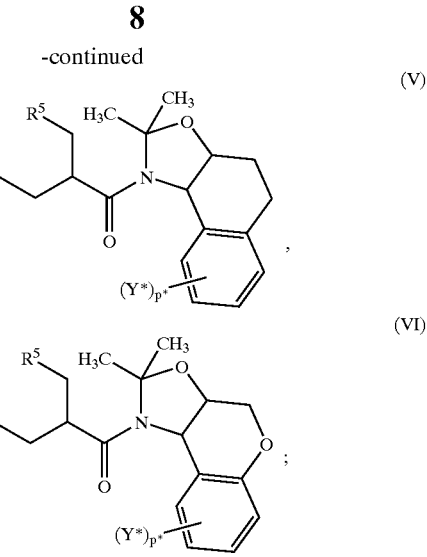

(V)

(VI)

wherein $R^5$ is $C_1$–$C_6$ alkyl, $C_3$–$C_6$ cycloalkyl, phenyl, naphthyl, or HetB; wherein the alkyl, cycloalkyl, phenyl, naphthyl, or HetB is optionally substituted with one or more substituents (e.g., from 1 to 4, or 1 to 3, or 1 or 2 substituents; or is mono-substituted) each of which is independently halogen, hydroxy, —$C_1$–$C_6$ haloalkyl, —O—$C_1$–$C_6$ alkyl, or —O—$C_1$–$C_6$ haloalkyl;
HetB is as earlier defined;
$R^6$ is —H, —$C_1$–$C_6$ alkyl, —$C_1$–$C_6$ haloalkyl, —$C_3$–$C_6$ cycloalkyl, or phenyl, wherein the phenyl is optionally substituted with one or more substituents (e.g., from 1 to 4, or 1 to 3, or 1 or 2 substituents; or is mono-substituted) each of which is independently halogen, —OH, —$C_1$–$C_6$ alkyl, —$C_1$–$C_6$ haloalkyl, —O—$C_1$–$C_6$ alkyl, or —O—$C_1$–$C_6$ haloalkyl;
each $Y^*$ is independently —H, halogen, —$C_1$–$C_4$ alkyl, —$C_1$–$C_4$ fluoroalkyl, or —O—$C_1$–$C_4$ alkyl; and
$p^*$ is an integer equal to zero, 1 or 2.

An aspect of the preceding class is an olefin which is:

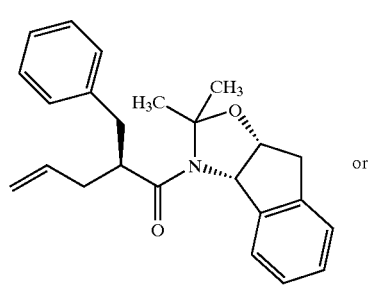

(1)

or

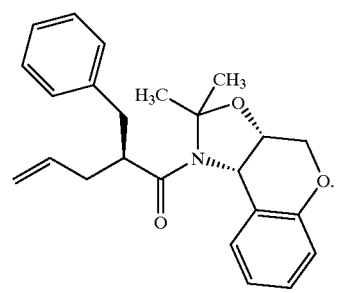

(3)

Additional embodiments of the present invention include, but are not limited to, olefins of Formula I wherein each of two or three or more of $R^1$, $R^2$, $R^3$, $R^4$, $R^a$, and $R^b$ is independently defined in accordance with its definition in one of the foregoing classes set forth above or a sub-class or aspect thereof. Any and all possible combinations of these variables in Formula I are embodiments within the scope of the present invention.

Unless expressly stated to the contrary, all ranges cited herein are inclusive. For example, a heteroaromatic ring described as containing from "1 to 4 heteroatoms" means the heteroaromatic ring can contain 1, 2, 3 or 4 heteroatoms.

When any variable (e.g., $R^a$ or $R^b$) occurs more than one time in Formula (I) or in any other formula defining an olefinic reactant suitable for use in the present invention, its definition on each occurrence is independent of its definition at every other occurrence.

The term "substituted" (e.g., as in "alkyl which is optionally substituted with one or more substituents . . . ") includes mono- and poly-substitution by a named substituent to the extent such single and multiple substitution (including multiple substitution at the same site) is chemically allowed.

It is also understood that combinations of substituents and/or variables set forth above in the formulas defining suitable olefin reactants are permissible only if such combinations result in olefins which are chemically stable under the conditions employed in the process of the invention and only if a stable iodohydroxylated olefin can be obtained in a detectable amount.

As stated earlier, the treatment step in the process of the present invention can be conducted over a wide pH range. At very low pH (e.g., less than about 1), however, the iodohydroxylation rate can be quite slow which can result in undesirably long reaction times and/or low conversions. While not wishing to be bound by theory, this relatively low iodohydroxylation rate at very low pH is believed to be due to a substantial reduction in the rate of hydrolysis of ICl and IBr to HOI. Accordingly, in one embodiment the treatment step is conducted at a pH of from about 2 to about 12 (e.g., from about 4 to about 11). The pH can be determined during the treatment step using a standard pH monitor inserted into or otherwise in contact with the reaction mixture.

The iodohydroxylation of certain olefin reactants can be pH-sensitive, in which case the pH can be controlled by use of a buffer or by addition of acid or base. For example, olefins of Formulas (II) to (VI) and/or intermediates formed therefrom in the treatment step can be unstable under acidic conditions. Accordingly, in one embodiment, the treatment step is conducted at a pH of from about 6 to about 12. In another embodiment, the treatment is conducted at a pH of from about 8 to about 10 (e.g., at a pH of about 9). In an aspect of each of the two preceding embodiments, the treatment is conducted on an olefin of Formula (II), (III), (IV), (V), or (VI). In another aspect of each of these embodiments, the pH is controlled by on-demand addition of base. The role of the base is to neutralize the HCl (or HBr) generated during the treatment step, wherein it is believed that the HCl (HBr) generation is due to ICl (IBr) hydrolysis to HOI and that base neutralization increases the rate of hydrolysis to HOI. Any organic or inorganic base which can be used to control the pH of the reaction mixture is suitable for use in the process of the invention. Suitable bases include those selected from the group consisting of alkali metal hydroxides, alkali metal carbonates, alkali metal oxides, $C_1$–$C_6$ alkoxides of alkali metals, alkaline earth metal hydroxides, alkaline earth metal oxides, tetra ($C_1$–$C_4$ alkyl) ammonium hydroxides, and tri-($C_1$–$C_4$ alkyl)amines. Exemplary bases include hydroxides, carbonates, and oxides of lithium, sodium and potassium; methoxides, ethoxides, and n- and iso-propoxides of lithium, sodium, and potassium; tetramethyl- and tetraethyl-ammonium hydroxide; triethylamine; and diisopropylethylamine. In one embodiment, the base is selected from the group consisting of alkali metal hydroxides. In an aspect of the preceding embodiment, the base is NaOH or KOH.

The treatment of the olefin with aqueous iodine monohalide (i.e., ICl or IBr) is suitably conducted at a temperature in a range of from about −25 to about 100° C. (e.g., from about −20 to about 95° C.), and is typically conducted at a temperature in the range of from about −10 to about 85° C. The iodohydroxylation reaction can often be conducted under relatively mild conditions. Accordingly, in one embodiment, the temperature is in a range of from about 10 to about 50° C. In another embodiment, the temperature is in a range of from about 15 to about 30° C. In still another embodiment, the temperature is from about 15 to about 25° C. (e.g., about 20° C.).

The olefin reactant is typically employed in the process of the invention in an organic solvent. The solvent can be any organic compound which under the treatment conditions employed is in the liquid phase, is chemically inert, and will dissolve, suspend, and/or disperse the olefin reactant. Particularly suitable for use in the process of the invention is any organic solvent which is not miscible with water under the conditions employed (e.g., at a given temperature and pressure) and thereby results in a mixture comprising two phases, one of which is an organic phase containing the olefin reactant and the other of which is an aqueous phase containing the iodine monohalide (i.e., ICl or IBr). If the olefin reactant is a liquid under the selected conditions, then the olefin can alternatively be employed neat and act as both organic solvent and substrate.

Suitable solvents include hydrocarbons, halohydrocarbons, ethers, esters, and nitriles. Typical solvents are selected from the group consisting of $C_3$–$C_{12}$ linear and branched alkanes, $C_1$–$C_{10}$ linear and branched halogenated alkanes, $C_5$–$C_{10}$ cycloalkanes, $C_6$–$C_{14}$ aromatic hydrocarbons, dialkyl ethers wherein each alkyl is independently a $C_1$–$C_6$ alkyl, $C_1$–$C_6$ linear and branched alkanes substituted with two —O—$C_1$–$C_6$ alkyl groups (which are the same or different), $C_4$–$C_8$ cyclic ethers and diethers, $C_6$–$C_8$ aromatic ethers, $C_1$–$C_6$ alkyl esters of $C_1$–$C_6$ alkylcarboxylic acids, $C_1$–$C_{10}$ alkyl alcohols, $C_2$–$C_6$ aliphatic nitriles, and $C_7$–$C_{10}$ aromatic nitriles.

In one embodiment, the solvent is selected from the group consisting of $C_1$–$C_6$ linear and branched halogenated alkanes, dialkyl ethers wherein each alkyl is independently a $C_1$–$C_4$ alkyl, $C_1$–$C_6$ linear and branched alkanes substituted with two —O—$C_1$–$C_4$ alkyl groups (which are the same or different), $C_4$–$C_6$ cyclic ethers and diethers, $C_1$–$C_4$ alkyl esters of $C_1$–$C_6$ alkylcarboxylic acids, and $C_2$–$C_4$ aliphatic nitriles. A class of organic solvents often employed in the process of the invention is any ester which is a $C_1$–$C_4$ alkyl ester of a $C_1$–$C_6$ alkylcarboxylic acid. A sub-class of this class consists of the $C_1$–$C_4$ alkyl acetates.

Exemplary solvents include pentanes (single isomers or mixtures thereof), hexanes (single isomers or mixtures), heptanes (single isomers or mixtures), and octanes (single isomers or mixtures), carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, xylene mixtures, ethylbenzene, ethyl ether, methyl t-butyl ether (MTBE), tetrahydrofuran (THF), dioxane, 1,2-dimethoxyethane (DME), anisole, phenetole, methyl acetate, ethyl propionate, ethyl acetate, n-propyl acetate, isopropyl acetate (IPAc), n-, t- and iso-butyl acetate, ethanol, n- and iso-propanol, tert-butyl alcohol, tert-amyl alcohol, acetonitrile, propionitrile, benzonitrile, and p-tolunitrile.

As indicated above, the reaction system typically contains an organic phase and an aqueous phase. Accordingly, in one embodiment of the present invention, the treatment is conducted with vigorous agitation. The term "vigorous agitation" refers herein to sufficient agitation (achieved, for example by stirring or shaking) of the mixture such that no phase separation can be observed visually between the aqueous and organic phases. In other words, although the aqueous and organic phases still exist, the agitation (e.g., stirring) is sufficient so that no visible phase separation can be detected by the naked eye.

The treatment is suitably conducted at ambient pressures, but super- and sub-atmospheric pressures can be employed. For example, when the olefin reactant is a gas under ambient conditions (e.g., low molecular weight alkenes such as ethylene and propylene), the treatment can be conducted under a pressure high enough to liquify the gas (e.g., for use as a neat liquid, or to increase the gaseous olefin's solubility in the organic solvent). On the other hand, an olefin reactant can be employed as a gas, preferably with agitation sufficient to provide intimate mixing of the gas with aqueous ICl or IBr.

The iodine monohalide can be employed in any proportion with respect to the olefin reactant which will result in the conversion of at least some of the olefin to iodohydroxylated product. Typically, however, the iodine monohalide is employed in a proportion which will optimize conversion of the olefin. In one embodiment, the amount of iodine monohalide employed in the treatment step is at least about 0.5 equivalent per equivalent of olefin, and is typically in the range of from about 1 to about 10 (e.g., from about 1 to about 5) equivalents per equivalent of olefin. In another embodiment, iodine monohalide is employed in an amount of from about 1 to about 2 (e.g., from about 1 to about 1.8) equivalents per equivalent of olefin. In an aspect of the preceding embodiment, the iodine monohalide is employed in an amount of from about 1.1 to about 1.5 equivalents (e.g., from about 1.2 to about 1.4 equivalents) per equivalent of olefin.

In a suitable procedure for conducting the process of the present invention, the olefin reactant in organic solvent is charged to a reactor vessel fitted with a means for monitoring and controlling pH and temperature, followed by addition of water and optionally a buffer. After bringing the contents of the reactor to the desired temperature, the iodine monohalide (i.e., ICl or IBr) is then added to the reactor vessel typically in the form of an aqueous solution while agitating (e.g., stirring) the reactor contents at a level sufficient to obtain intimate mixing of the organic and aqueous phases. If a basic reaction environment, base can be added concurrently with addition of the iodine monohalide in order to maintain the pH at the desired level. Upon completion of the iodine monohalide addition, the mixture is maintained at a suitable temperature (and optionally also maintained at a suitable pH) until the iodohydroxylation is complete or, alternatively, until a desired amount of conversion is achieved. The reaction can be quenched by addition of a reducing agent (e.g., a dilute sodium bisulfite aqueous solution), and the organic phase separated from the aqueous phase. The iodohydrin product can then be recovered (i.e., isolated) from the organic phase by conventional techniques (e.g., by chromatography, by fractional distillation to recover a liquid product, or by concentrating and/or cooling to precipitate a solid product). In the case where the iodohydrin product is an intermediate, the iodohydrin need not be isolated, but can instead be left in the organic phase or solvent switched into a different organic solvent for use in the next step of the synthesis.

The iodine monohalide and water can be separately added to the reactor vessel either concurrently or consecutively in either order, with subsequent formation of an aqueous iodine monohalide solution in the reactor. Direct addition of a pre-mixed aqueous iodine monohalide solution is preferred, however, because it eliminates an addition line and avoids potential difficulties in metering ICl (a solid or oil with melting point =27° C.) or IBr (solid with melting point =40° C.) into the reactor. The aqueous solution can be prepared for immediate use in the process of the invention simply by dissolving the desired amount of ICl or IBr in water and then adding the solution into the reactor vessel. A stabilized solution of the iodine monohalide can be prepared and stored for long periods (weeks or months) for future use in the process of the invention. A stabilized ICl solution is a low-pH aqueous-HCl—NaCl solution. Similarly, a stabilized IBr solution is a low-pH aqueous HBr—NaBr solution. While not wishing to be bound by theory, it is believed that in this solution ICl, for example, exists stably and predominantly in the form of $ICl_2^-$ (see Wang et al., *J. Am. Chem. Soc.* 1989, 111: 7838–7844). Olefin iodohydroxylation can occur by contacting this solution with (e.g., adding this solution to) an olefin and, if necessary, adjusting the pH to the basic range. The overall scheme for HOI production using the stabilized ICl solution is as follows, wherein pH control can be optionally employed in both steps:

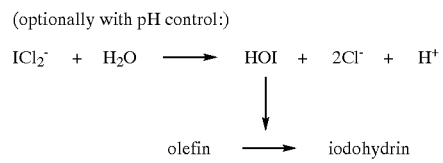

The iodine monohalide can suitably be added all at once at the start, or intermittently or continuously as the iodohydroxylation proceeds. Intermittent or continuous addition of iodine monohalide is preferred. The monohalide (ICl or IBr) is suitably added to the mixture at a rate of from about 0.2 to about 30 equivalents of iodine monohalide per equivalent of olefin per hour, and is typically added at a rate of from about 0.3 to about 10 equivalents (e.g., 0.5 to 5 equivalents) per equivalent of olefin per hour. In one embodiment, the iodine monohalide addition is continuous until the desired total amount of ICl or IBr has been charged to the reaction mixture. In an aspect of this embodiment, the iodine monohalide is added continuously at a rate of from about 0.5 to 5 equivalents per equivalent of olefin per hour. In another aspect of this embodiment, the iodine monohalide is added continuously at a rate of from about 0.5 to 2 equivalents (e.g., from about 1 to about 1.8 equivalents) per equivalent of olefin per hour.

The treatment time can vary widely depending upon, inter alia, the temperature, the choice of olefin reactant, and the relative amounts of iodine monohalide and olefin, but it is typically in the range of from about 0.05 to about 24 hours.

If desired, the progress of the iodohydroxylation can be followed by monitoring the disappearance of the olefin and/or the appearance of the iodohydrin product using TLC, HPLC, NMR or GC.

The present invention also includes a process for preparing an iodohydrin of Formula (VII):

(VII)

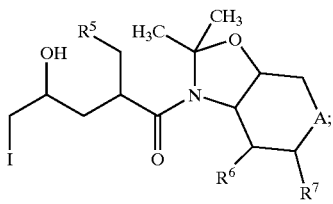

which comprises treating an olefin of Formula (II):

(II)

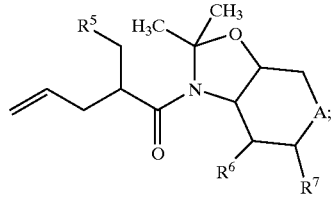

in an organic solvent with an aqueous solution of an iodine monohalide at a pH in a range of from about 6 to about 12 to obtain iodohydrin VII, wherein:
the iodine monohalide selected from iodine monochloride and iodine monobromide;
and wherein in Formulas (II) and (VII):
A is absent, $CH_2$, O, or S;
$R^5$ is $C_1$–$C_6$ alkyl, $C_3$–$C_6$ cycloalkyl, phenyl, naphthyl, or HetB; wherein the alkyl, cycloalkyl, phenyl, naphthyl, or HetB is optionally substituted with one or more substituents (e.g., from 1 to 4, or 1 to 3, or 1 or 2 substituents; or is mono-substituted) each of which is independently halogen, hydroxy, —$C_1$–$C_6$ haloalkyl, —O—$C_1$–$C_6$ alkyl, or —O—$C_1$–$C_6$ haloalkyl;
HetB in $R^5$ is a 5- or 6-membered monocyclic aromatic ring containing from 1 to 4 heteroatoms independently selected from N, O and S; and
$R^6$ and $R^7$ are each independently —H, —$C_1$–$C_6$ alkyl, —$C_1$–$C_6$ haloalkyl, —$C_3$–$C_6$ cycloalkyl, or aryl, wherein aryl is selected from phenyl and naphthyl, and is optionally substituted with one or more substituents (e.g., from 1 to 4, or 1 to 3, or 1 or 2 substituents; or is mono-substituted) each of which is independently halogen, —OH, —$C_1$–$C_6$ alkyl, —$C_1$–$C_6$ haloalkyl, —O—$C_1$–$C_6$ alkyl, or —O—$C_1$–$C_6$ haloalkyl; or alternatively
$R^6$ and $R^7$ together with the carbons to which each is attached form a fused benzene ring which is optionally substituted with one or more substituents (e.g., from 1 to 4, or 1 to 3, or 1 or 2 substituents; or is mono-substituted) each of which is independently halogen, —OH, —$C_1$–$C_6$ alkyl, —$C_1$–$C_6$ haloalkyl, —O—$C_1$–$C_6$ alkyl, or —O—$C_1$–$C_6$ haloalkyl.

Embodiments of this process include the process as just described incorporating one or more of the features (a), (b), (c), (d), (e), (f1) or (f2), and (g) as follows:
(a) the treatment is conducted at a pH of from about 7 to about 10 (or from about 8 to about 10);
(b) the pH of the mixture is controlled by on-demand addition of base (e.g., an alkali metal hydroxide such as NaOH);
(c) the treatment is conducted at a temperature in a range of from about −10 to about 85° C. (or from about 10 to about 50° C., or from about 15 to about 30° C.);
(d) the iodine monohalide (e.g., ICl) is employed in an amount of from about 1 to about 5 equivalents (or from about 1 to about 2 equivalents, or from about 1 to about 1.8 equivalents) per equivalent of olefin II;
(e) the treatment is conducted with vigorous agitation;
(f1) the organic solvent is selected from the group consisting of $C_1$–$C_6$ linear and branched halogenated alkanes, dialkyl ethers wherein each alkyl is independently a $C_1$–$C_4$ alkyl, $C_1$–$C_6$ linear and branched alkanes substituted with two —O—$C_1$–$C_4$ alkyl groups (which are the same or different), $C_4$–$C_6$ cyclic ethers and diethers, $C_1$–$C_4$ alkyl esters of $C_1$–$C_6$ alkylcarboxylic acids, and $C_2$–$C_4$ aliphatic nitriles;
(f2) the organic solvent is a $C_1$–$C_4$ alkyl acetate (e.g., IPAc); and
(g) the olefin is:

(III)

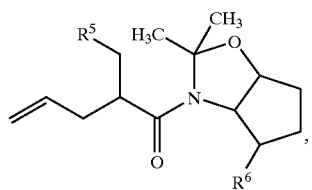

(IV)

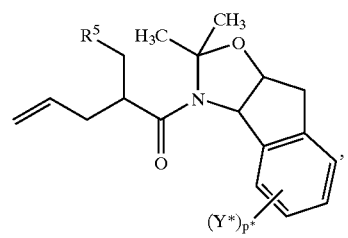

(V)

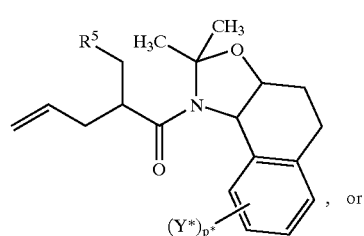

, or (VI)

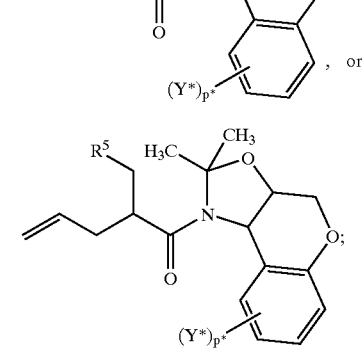

wherein:
$R^5$ is $C_1$–$C_6$ alkyl, $C_3$–$C_6$ cycloalkyl, phenyl, naphthyl, or HetB; wherein the alkyl, cycloalkyl, phenyl, naphthyl, or HetB is optionally substituted with one or more substituents (e.g., from 1 to 4, or 1 to 3, or 1 or 2 substituents; or is mono-substituted) each of which is independently halogen, hydroxy, —$C_1$–$C_6$ haloalkyl, —O—$C_1$–$C_6$ alkyl, or —O—$C_1$–$C_6$ haloalkyl;
HetB in $R^5$ is a 5- or 6-membered monocyclic aromatic ring containing from 1 to 4 heteroatoms independently selected from N, O and S; and
$R^6$ is —H, —$C_1$–$C_6$ alkyl, —$C_1$–$C_6$ haloalkyl, —$C_3$–$C_6$ cycloalkyl, or phenyl, wherein the phenyl is optionally substituted with one or more substituents (e.g., from 1 to 4, or 1 to 3, or 1 or 2 substituents; or is mono-substituted) each of which is independently halogen, —OH, —$C_1$-$C_6$ alkyl, —$C_1$-$C_6$ haloalkyl, —O—$C_1$-$C_6$ alkyl, or —O—$C_1$-$C_6$ haloalkyl;

each Y* is independently —H, halogen, —$C_1$-$C_4$ alkyl, —$C_1$-$C_4$ fluoroalkyl, or —O—$C_1$-$C_4$ alkyl; and p* is an integer equal to zero, 1 or 2.

The present invention also includes a process for preparing iodohydrin 2 or 4:

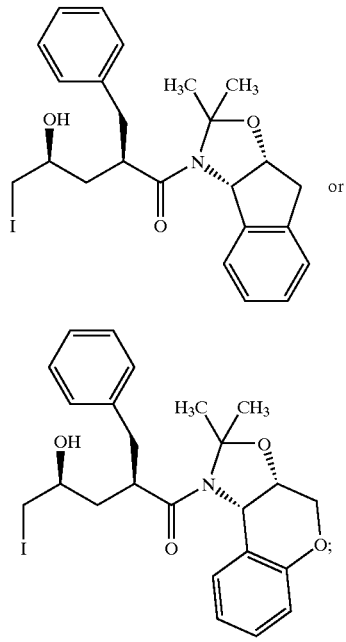

which comprises treating olefin 1 or 3:

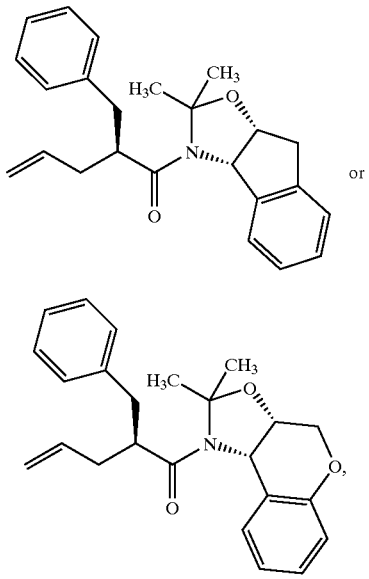

in an organic solvent with an aqueous solution of iodine monohalide at a pH in a range of from about 6 to about 12 to obtain iodohydrin 2 or 4; wherein the iodine monohalide is ICl or IBr.

Olefin 1 (also referred to in the art as an allyl acetonide) can be prepared as described in Example 1 of U.S. Pat. No. 5,728,840. Olefin (or allyl acetonide) 3 can be prepared as described in Example 1 of WO 01/38332.

Embodiments of this process include the process as just described incorporating one or more of the features (a), (b), (c), (d), (e), and (f1) or (f2) set forth above.

Still other embodiments of the present invention include the process as originally defined and described above and any embodiments or aspects thereof as heretofore defined and described, further comprising isolating (alternatively referred to as recovering) the iodohydrin product from the treatment mixture.

Iodohydrins of Formula (VII) are useful as intermediates in the preparation of HIV protease inhibitors as may be seen by reference to U.S. application Ser. No. 09/718,223 (filed Nov. 21, 2000) and to WO 01/38332, the disclosures of which are herein incorporated by reference in its entireties. More particularly, iodohydrin 2 can be converted into indinavir as described in U.S. Pat. No. 5,728,840 (see, e.g., Examples 1 to 8), and iodohydrin 4 can be used as an intermediate in the preparation of a series of HIV protease inhibitors as described in U.S. Ser. No. 09/718,223 and WO 01/38332 (see, e.g., Example 1 and subsequent examples). The following scheme depicts the preparation of indinavir via iodohydrin 2:

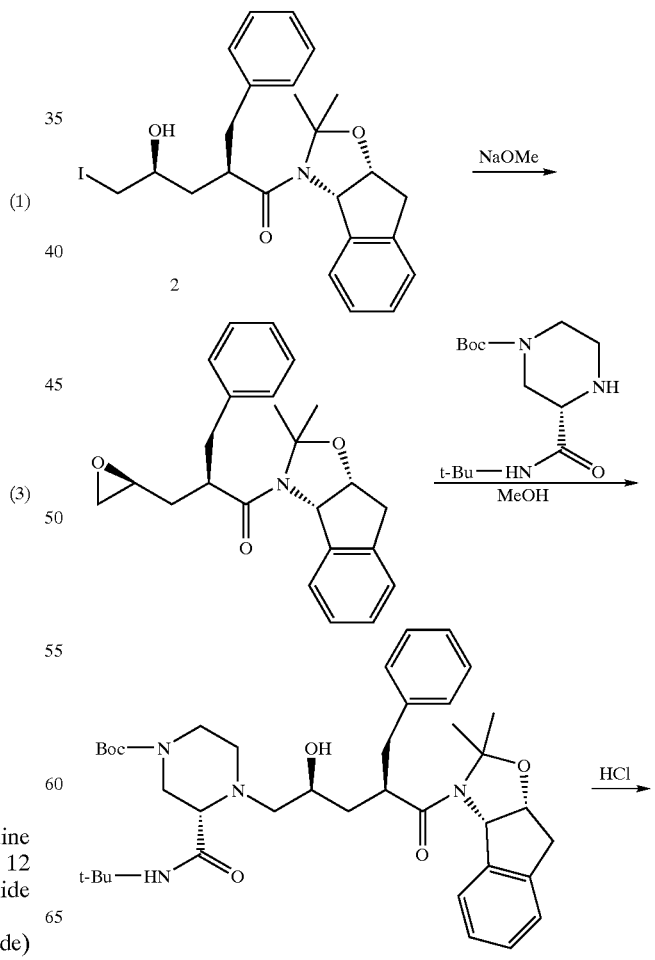

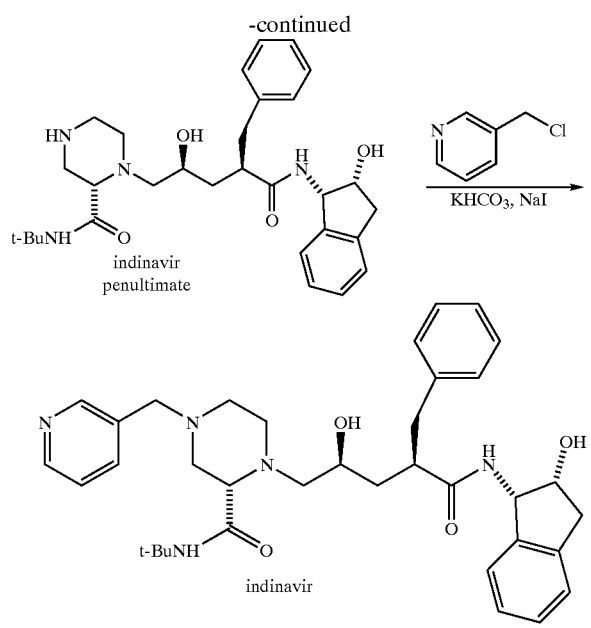

The terms "iodohydroxylated olefin" and "iodohydrin" are used herein interchangeably.

As used herein, the term "$C_{1-20}$ alkyl" (or "$C_1-C_{20}$ alkyl") means linear or branched chain alkyl groups having from 1 to 20 carbon atoms. The term "$C_{1-6}$ alkyl" (or "$C_1-C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. Similar terms such as "$C_{1-10}$ alkyl" and "$C_{1-4}$ alkyl" have analogous meanings.

The term "$C_{2-20}$ alkenyl" (or "$C_2-C_{20}$ alkenyl") means linear or branched chain alkenyl groups having from 2 to 20 carbon atoms. The term "$C_{2-10}$ alkenyl" has an analogous meaning and includes all of the decenyl, nonenyl, octenyl, heptenyl, hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-6}$ alkenyl" have an analogous meaning.

The term "$C_{3-8}$ cycloalkyl" (or "$C_3-C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). Similar terms such as "$C_{3-6}$ cycloalkyl" have an analogous meaning.

The term "$C_{5-10}$ cycloalkenyl" (or "$C_5-C_{10}$ cycloalkenyl") means a cyclic ring of an alkene having five to ten total carbon atoms (i.e., cyclopentenyl, cyclohexenyl, cycloheptenyl, cyclooctenyl, cyclononenyl, or cyclodecenyl). Similar terms such as "$C_{5-8}$ cycloalkenyl" have an analogous meaning.

The term "$C_{5-10}$ cycloalkadienyl" (or "$C_5-C_{10}$ cycloalkadienyl") means a cyclic ring of an alkadiene having five to ten total carbon atoms (i.e., cyclopentadienyl, cyclohexadienyl, cycloheptadienyl, cyclooctadienyl, cyclononadienyl, or cyclodecadienyl).

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1-C_6$ haloalkyl" or "halogenated $C_1-C_6$ alkyl") means a $C_1$ to $C_6$ linear or branched alkyl group as defined above with one or more halogen substituents. The term "$C_{1-4}$ haloalkyl" has an analogous meaning. The term "$C_{1-4}$ fluoroalkyl" (which may alternatively be referred to as "$C_1-C_4$ fluoroalkyl" or "fluorinated $C_1-C_4$ alkyl") has an analogous meaning except that the halogen substituents are restricted to fluoro. Suitable fluoroalkyls include the series $(CH_2)_{0-3}CF_3$.

The term "aryl" as used herein refers to any ring which is (i) an aromatic carbocyclic ring optionally substituted with 1 or 2 other aromatic carbocyclic rings or (ii) an aromatic carbocyclic fused ring system optionally substituted with 1 or 2 aromatic carbocyclic rings. The fused ring system contains two or more carbocyclic rings in which each ring shares two adjacent carbon atoms with at least one other ring. A subset of aryl groups particularly suitable for defining olefin reactants employed in the process of the invention includes those selected from phenyl, biphenyl, naphthyl, anthryl, and phenanthryl. Another particularly suitable subset of aryl groups is phenyl and naphthyl. Still another particularly suitable subset is phenyl per se.

The term "heterocycle" refers to any ring which is (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; and wherein the monocyclic ring, bicyclic ring system, or tricyclic ring system contains from 1 to 6 heteroatoms independently selected from N, O and S.

A subset of heterocycles suitable for defining olefin reactants employed in the process of the invention includes the set of saturated heterocyclic rings. The term "saturated heterocyclic ring" refers to a 4- to 7-membered saturated monocyclic ring which contains one or more heteroatoms independently selected from N, O and S. Representative examples include piperidinyl, piperazinyl, azepanyl (i.e.,

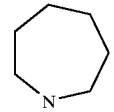

pyrrolidinyl, pyrazolidinyl, imidazolidinyl, oxazolidinyl, isoxazolidinyl, morpholinyl, thiomorpholinyl, thiazolidinyl, isothiazolidinyl, tetrahydrothienyl, tetrahydrofuryl (or tetrahydrofuranyl), thiazinanyl (e.g., 1,2-thiazinanyl

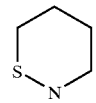

thiadiazinanyl (e.g., 1,2,6-thiadiazinanyl

and dioxanyl.

Heteroaromatic rings form another subset of the heterocycles that is suitable for defining olefin reactants of the present invention. The term "heteroaromatic ring" refers a 5- or 6-membered monocyclic aromatic ring containing one or more (e.g., from 1 to 4) heteroatoms independently selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

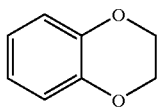

and benzo-1,3-dioxolyl (i.e.,

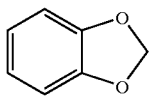

Representative examples of tricyclic heterocycles include phenothiazinyl, carbazolyl, beta-carbolinyl, tetrahydro-beta-carbolinyl, acridinyl, phenazinyl, and phenoxazinyl.

The following examples serve only to illustrate the invention and its practice. The examples are not to be construed as limitations on the scope or spirit of the invention.

EXAMPLE 1

Iodohydroxylation of Allyl Acetonide 1 Using ICl

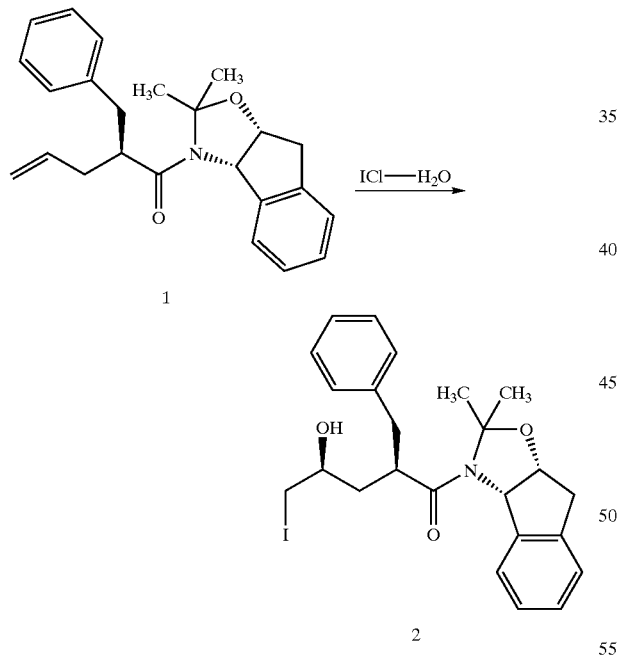

Run A:

The iodohydroxylation of 1 was carried out in a Mettler RC-1 reaction calorimeter (reactor volume: 1L), which provides computer control over the pH and dosing control functions. To the top charge opening in the reactor was added 200 mL of allyl acetonide 1 in IPAc having an assay of 148 g/L (0.082 mole), followed by the addition of 121 mL of DI water and 0.45 g of $NaHCO_3$. The reactor stirrer was set to 800 rpm (which provided vigorous agitation as defined herein), and the reactor temperature adjusted to 20° C. while purging the system with nitrogen. A pH control probe was inserted into the reactor, and the system was purged with nitrogen to ensure removal of air. To the reactor was then added 1.2 equivalents (18.9 mL) of 5.2 M ICl solution over a time interval of 60 minutes. (Note: The ICl solution (5.2 M) was prepared by dissolving ICl (50.6 g), a solution of concentrated HCl (2.9 g; 37% aqueous), and NaCl (14.02 g) in distilled water (20 mL). The solution was then diluted to a total volume of 60 mL with distilled water.) The ICl solution was added using a syringe pump at an addition rate of 0.31 mL/min. NaOH (1M) was added concurrently with the addition of the ICl at a rate such that the reactor contents were maintained at a pH of 9.0. The NaOH addition was performed by the control loop of the Mettler RC-1 computerized system. The reaction was continued for a period of 10 minutes after complete addition of the ICl solution. LC analysis showed 100% conversion of 1 and with a 95% yield of iodohydrin 2.

Run B:

A second iodohydroxylation of 1 was conducted using the same reactor, procedure and conditions described in Run A, except that the reactor stirrer was operated at 1500 rpm (which provided vigorous agitation as defined herein). LC analysis of a grab sample 10 min after complete addition of the ICl solution showed 100% conversion of 1 with a 95% yield of iodohydrin 2.

EXAMPLE 2

Iodohydroxylation of Allyl Acetonide 3 Using ICl

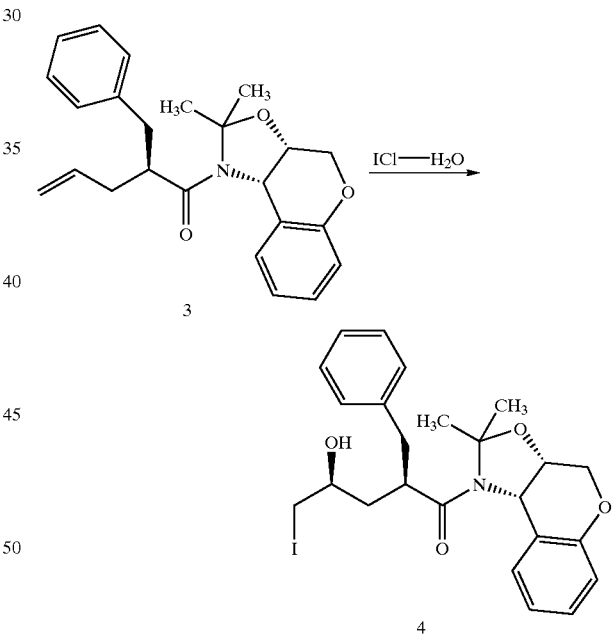

The iodohydroxylation of 3 was conducted using the Mettler RC-1 reaction calorimeter described in Example 1. 200 mL of allyl acetonide 3 in IPAc having an assay of 109 g/L (0.058 mole) were added to the top charge opening in the reactor, followed by the addition of 121 mL of DI water and 0.45 g of $NaHCO_3$. The reactor stirrer was set to 800 rpm (which provided vigorous agitation as defined herein) and the reactor temperature was adjusted to 20° C. while purging the system with nitrogen. A pH control probe was inserted into the reactor and the system was purged with nitrogen to ensure removal of air. To the reactor was then added 1.2 equivalents (13.3 mL) of 5.2 M ICl solution over a time interval of 60 minutes. The ICl solution was added using a syringe pump at an addition rate of 0.22 mL/min. NaOH (1M) was added concurrently with the addition of the ICl at a rate such that the reactor contents were maintained at a pH of 9.0. The NaOH addition was performed by the control loop of the Mettler RC-1 computerized system. The reaction was continued for a period of 10 minutes after complete addition of the ICl solutions. LC analysis showed 100% conversion of 3 and greater than 90% yield of iodohydrin 4.

EXAMPLE 3

Iodohydroxylation of Allyl Acetonide 1 Using NaOCl/NaI

Run A:

The iodohydroxylation of allyl acetonide 1 via NaOCl/NaI was conducted in the reactor system described in Example 1 as follows: Allyl acetonide 1 in IPAc (200 mL; 148 g/L (=0.082 mole)) was added to the top charge opening in the reactor, followed by the addition of 121 mL of DI water and 0.45 g of NaHCO$_3$. The reactor stirrer was set at 800 rpm (which provided vigorous agitation as defined herein), and the reactor temperature adjusted to 20° C. A pH control probe was inserted into the reactor. To the reactor was added 2.0 equivalents (76.3 g) of 16 wt. % aqueous sodium hypochlorite solution and 1.8 equivalents (34.41 g, 22.82 mL) of 57% aqueous NaI solution over 60 minutes. The NaI solution was added using a syringe pump at an addition rate of 0.380 mL/min. The NaOCl solution was added by means of a diaphragm pump, adjusted to provide a uniform addition rate. Concurrent with the addition of the NaOCl and NaI solutions, H$_2$SO$_4$ was added using the control loop of the Mettler RC-1 system at a rate such that the reactor contents were maintained at a pH of 9.0. LC analysis of a grab sample 10 min after the completing the addition of the NaOCl and NaI solutions showed 100% conversion of acetonide 1 and a 95% yield of iodohydrin 2.

Run B:

A second iodohydroxylation of 1 using NaOCl/NaI was conducted using the same reactor, procedure and conditions as described in Run A, except that the reactor stirrer was operated at 1500 rpm (which provided vigorous agitation as defined herein). LC analysis of a grab sample 10 minutes after complete addition of the NaOCl and NaI solutions showed 75% conversion of 1 and a 71% yield of iodohydrin 2.

Table 1 below presents the percent conversions of allyl acetonide 1 to iodohydrin 2 obtained in Examples 1 and 3 as a function of reactor stirrer speed. The stirrer speed is a measure of the degree of agitation and mixing of the reaction mixture. The results show that the NaOCl/NaI process exhibits a mixing sensitivity which is absent in the ICl process. These results indicate that the ICl process of the invention is more scaleable than the NaOCl/NaI process, which is a significant process advantage.

TABLE 1

| Example No. | Process | Stirring Speed (rpm) | % Yield % Conversion |
|---|---|---|---|
| 1-A | ICl | 800 | 95 (100) |
| 1-B | " | 1500 | 95 (100) |
| 3-A | NaOCl/NaI | 800 | 95 (100) |
| 3-B | " | 1500 | 71 (75) |

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing an iodohydroxylated olefin which comprises treating an olefin with an aqueous solution of an iodine monohalide selected from iodine monochloride and iodine monobromide, wherein the treatment involves contact of an organic phase containing the olefin with an aqueous phase containing the iodine monohalide solution.

2. The process according to claim 1, wherein the treatment is conducted at a temperature in a range of from about −25 to about 100° C.

3. The process according to claim 1, wherein the olefin is employed as a neat liquid or in an organic solvent.

4. The process according to claim 3, wherein the olefin is in an organic solvent selected from the group consisting of hydrocarbons, halohydrocarbons, ethers, esters, and nitriles.

5. The process according to claim 1, wherein the treatment is conducted with vigorous agitation.

6. The process according to claim 1, wherein the iodine monohalide is employed in an amount of from 1 to about 10 equivalents per equivalent of olefin.

7. The process according to claim 1, wherein the pH is in a range of from about 2 to about 12.

8. The process according to claim 7, wherein the pH is in a range of from about 6 to about 12.

9. The process according to claim 8, wherein the pH is controlled by on-demand addition of base.

10. The process according to claim 1, wherein the aqueous solution of iodine monohalide is added at a rate of from about 0.2 to about 30 equivalents of iodine monohalide per equivalent of olefin per hour.

11. The process according to claim 1, wherein the olefin is of Formula (I):

wherein each of R$^1$, R$^2$, R$^3$ and R$^4$ is independently:

(1) —H,
(2) —CO$_2$R$^a$,
(3) —C(═O)R$^a$,
(4) —C(═O)N(R$^a$R$^b$),
(5) —CN,
(6) C$_{1-20}$ alkyl,
(7) C$_{2-20}$ alkenyl,
(8) C$_{3-8}$ cycloalkyl,
(9) C$_{5-8}$ cycloalkenyl,
(10) aryl, or
(11) heterocycle,
(12) C$_{1-20}$ alkyl substituted with from 1 to 3 substituents each of which is independently C$_{3-8}$ cycloalkyl, C$_{5-8}$ cycloalkenyl, aryl, or heterocycle,
(13) C$_{2-20}$ alkenyl substituted with from 1 to 3 substituents each of which is independently C$_{3-8}$ cycloalkyl, C$_{5-8}$ cycloalkenyl, aryl, or heterocycle,
(14) C$_{1-20}$ alkyl substituted with —C(═O)-aryl or —(═O)-heterocycle, or
(15) C$_{2-20}$ alkenyl substituted with —C(═O)-aryl or —C(═O)-heterocycle;

wherein the alkyl in (6) or (12) or (14) or the alkenyl in (7) or (13) or (15) is optionally substituted with one or more substituents each of which is independently halogen, —OH, —CN, —O—C$_{1-6}$ alkyl, —O—C$_{1-6}$ haloalkyl, —C(=O)R$^a$, —CO$_2$R$^a$, —S(O)$_n$R$^a$, —N(R$^a$R$^b$), —C(=O)N(R$^a$R$^b$), N(R$^a$)C(=O)—N (R$^a$R$^b$), —C(=O)—C$_{1-6}$ alkyl-N(R$^a$R$^b$), N(R$^a$)—C (=O)—C$_{1-6}$ alkyl-N(R$^a$R$^b$), —N(R$^a$)SO$_2$R$^b$, or —SO$_2$N(R$^a$R$^b$);

wherein the cycloalkyl in (8) or (12) or (13), the cycloalkenyl (9) or (12) or (13), or the aryl in (10) or (12) or (13) or (14) or (15) is optionally substituted with one or more substituents each of which is independently halogen, —OH, —CN, —C$_{1-6}$ alkyl, —C$_{1-6}$ haloalkyl, —O—C$_{1-6}$ alkyl, —O—C$_{1-6}$ haloalkyl, —C(=O)R$^a$, —CO$_2$R$^a$, —S(O)$_n$R$^a$, —N(R$^a$R$^b$), —C(=O)N(R$^a$R$^b$), —C(=O)—C$_{1-6}$ alkyl-N(R$^a$R$^b$), phenyl, —C$_{1-6}$ alkyl-phenyl, HetA, or —C$_{1-6}$ alkyl-HetA; and wherein the heterocycle (11) or (12) or (13) or (14) or (15) is optionally substituted with one or more substituents each of which is independently halogen —OH, —CN, —C$_{1-6}$ alkyl, —C$_{1-6}$ haloalkyl, —O—C$_{1-6}$ alkyl, —O—C$_{1-6}$ haloalkyl, —C(=O)R$^a$, —CO$_2$R$^a$, —S(O)$_n$R$^a$, —N(R$^a$R$^b$), —C(=O)N(R$^a$R$^b$), —C(=O)—C$_{1-6}$ alkyl-N(R$^a$R$^b$), phenyl, —C$_{1-6}$ alkyl-phenyl, —C$_{3-8}$ cycloalkyl, —C$_{1-6}$ alkyl-C$_{3-8}$ cycloalkyl, or oxo;

or alternatively R$^1$ and R$^3$ are each independently as defined above, and R$^2$ an R$^4$ together with each of the carbon atoms of the carbon-carbon double bond form C$_{5-10}$ cycloalkenyl or C$_{5-10}$ cycloalkadienyl, either of which is optionally substituted with one or more substituents each of which is independently halogen, C$_{1-6}$ alkyl, C$_{1-6}$ haloalkyl, —O—C$_{1-6}$ alkyl, —O—C$_{1-6}$ haloalkyl, or hydroxy;

or alternatively R$^1$ and R$^2$ are each independently as defined above, and R$^3$ an R$^4$ together with the carbon atom of the carbon-carbon double bond to which they are both attached form C$_{5-10}$ cycloalkyl or C$_{5-10}$ cycloalkenyl, either of which is to optionally substitute with one or more substituents each of which is independently halogen, C$_{1-6}$ alkyl, C$_{1-6}$ haloalkyl, —O—C$_{1-6}$ alkyl, —O—C$_{1-6}$ haloalkyl, or hydroxy;

each aryl is independently (i) an aromatic carbocyclic ring optionally substitute with 1 or 2 other aromatic carbocyclic rings or (ii) an aromatic carbocyclic fused ring system optionally substituted with 1 or 2 aromatic carbocyclic rings;

each heterocycle is independently (i) a 4- to 8-membered, saturated or unsaturated monocyclic ring, (ii) a 7- to 12-membered bicyclic ring system, or (iii) 11 to 16-membered tricyclic ring system; wherein each ring in (ii) or (iii) is independent of or fused to the other ring or rings and each ring is saturated or unsaturated; and wherein the monocyclic ring, bicyclic ring system, or tricyclic ring system contains from 1 to 6 heteroatoms independently selected from N, O and S;

each HetA is independently:
(i) a 4- to 7-membered saturated heterocyclic ring containing from 1 to 4 heteratoms selected from N, O and S, wherein the saturated heterocyclic ring is optionally substituted with from 1 to 3 substituents each of which is independently halogen, —C$_{1-4}$ alkyl, or oxo, or
(ii) a 5- or 6-membered heteroaromatic ring containing from 1 to 4 heteroatoms independently selected from N, O and S, where the heteroaromatic ring is optionally substituted with from 1 to 3 substituents each of which is independently halogen, —C$_{1-4}$ alkyl, or —O—C$_{1-4}$ alkyl;

each n is an integer independently equal to zero, 1 or 2; and each R$^a$ and R$^b$ is independently —H or —C$_{1-6}$ alkyl.

12. A process for preparing an iodohydroxylated olefin which comprises treating an olefin with an aqueous solution of an iodine monohalide selected from iodine monochloride and iodine monobromide, wherein the olefin is of Formula (II):

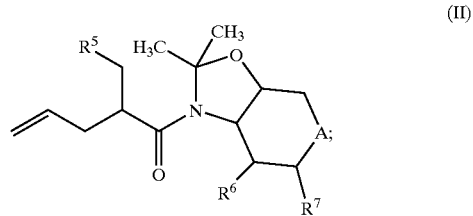

(II)

wherein A is absent, CH$_2$, O, or S;

R$^5$ is C$_1$–C$_6$ alkyl, C$_3$–C$_6$ cycloalkyl, phenyl, naphthyl, or HetB; wherein the alkyl, cycloalkyl, phenyl, naphthyl, or HetB is optionally substituted with one or more substituents each of which is independently halogen, hydroxy, —C$_1$–C$_6$ haloalkyl, —O—C$_1$–C$_6$ alkyl, or —O—C$_1$–C$_6$ haloalkyl;

HetB in R$^5$ is a 5- or 6-membered monocyclic aromatic ring containing from 1 to 4 heteroatoms independently selected from N, O and S; and R$^6$ and R$^7$ are each independently —H, —C$_1$–C$_6$ alkyl, —C$_1$–C$_6$ haloalkyl, —C$_3$–C$_6$ cycloalkyl, or aryl, wherein aryl is selected from phenyl and naphthyl, and is optionally substituted with one or more substituents each of which is independently halogen, —H, —C$_1$–C$_6$ alkyl, —C$_1$–C$_6$ haloalkyl, —O—C$_1$–C$_6$ alkyl, or —O—C$_1$–C$_6$ haloalkyl; or alternatively R$^6$ and R$^7$ together with the carbons to which each is attached form a fused benzene ring which is optionally substituted with one or more substituents each of which is independently halogen, —OH, —C$_1$–C$_6$ alkyl, —C$_1$–C$_6$ haloalkyl, —O—C$_1$–C$_6$ alkyl, or —O—C$_1$–C$_6$ haloalkyl.

13. The process according a claim 12 wherein the olefin is:

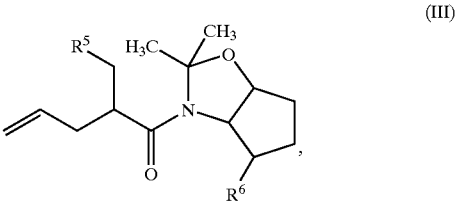

(III)

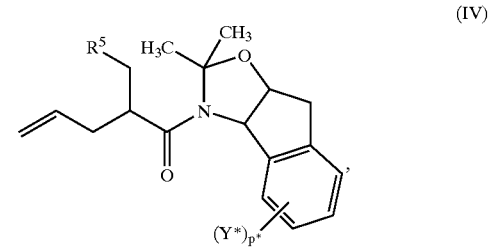

(IV)

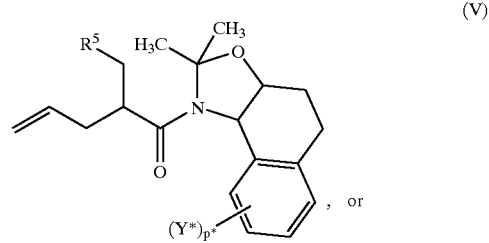

(V), or

-continued (VI)

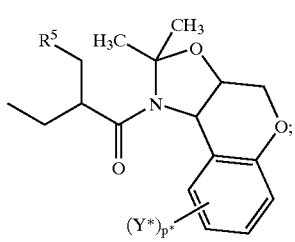

wherein:

$R^5$ is $C_1$–$C_6$ alkyl, $C_3$–$C_6$ cycloalkyl, phenyl, naphthyl, or HetB; wherein the alkyl, cycloalkyl, phenyl, naphthyl, or HetB is optionally substituted with one or more substituents each of which is independently halogen, hydroxy, —$C_1$–$C_6$ haloalkyl, —O—$C_1$–$C_6$ alkyl, or —O—$C_1$–$C_6$ haloalkyl;

HetB in $R^5$ is a 5- or 6-membered monocyclic aromatic ring containing from 1 to 4 heteroatoms independently selected from N, O and S; and $R^6$ is —H, —$C_1$–$C_6$ alkyl, —$C_1$–$C_6$ haloalkyl, —$C_3$–$C_6$ cycloalkyl or phenyl, wherein the phenyl is optionally substituted with one or more substituents each of which is independently halogen, —OH, —$C_1$–$C_6$ alkyl, —$C_1$–$C_6$ haloalkyl, —O—$C_1$–$C_6$ alkyl, or —O—$C_1$–$C_6$ haloalkyl;

each $Y^*$ is independently —H, halogen, —$C_1$–$C_4$ alkyl, —$C_1$–$C_4$ fluoroalkyl, or —O—$C_1$–$C_4$ alkyl; and $p^*$ is an integer equal to zero, 1 or 2.

14. The process according o claim 13, wherein the olefin is (1)

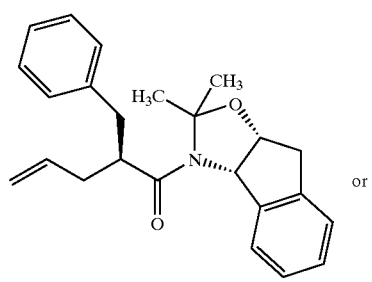

or (3)

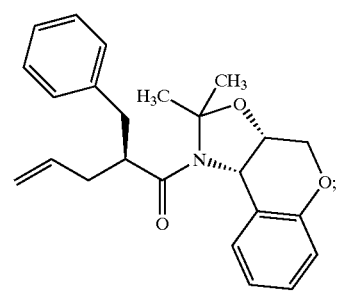

and the obtained iodohydroxylated olefin is (2)

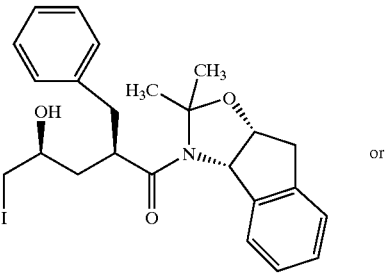

or (4)

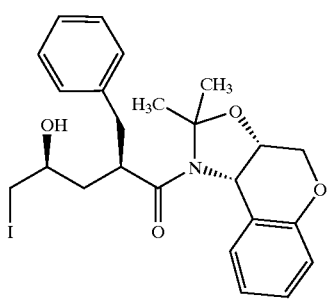

15. The process according to claim 12, wherein the pH is in a range of from about 6 to about 12.

16. A process for preparing an iodohydrin of Formula (VII):

(VII)

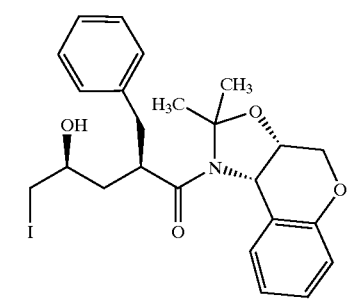

which comprises treating an olefin of Formula (II):

(II)

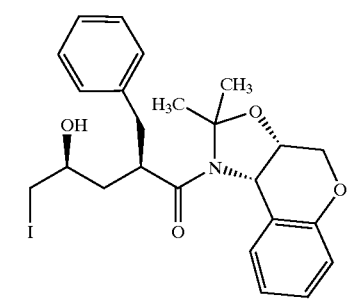

in an organic solvent with an aqueous solution of an iodine monohalide at a pH in a range of from about 6 to about 12 to obtain iodohydrin VII, wherein:
the iodine monohalide selected from iodine monochloride an iodine monobromide;
and wherein in Formulas (II) and (VII):
A is absent, $CH_2$, O, or S;
$R^5$ is $C_1$–$C_6$ alkyl, $C_3$–$C_6$ cycloalkyl, phenyl, naphthyl, or HetB; wherein the alkyl, cycloalkyl, phenyl, naphthyl, or HetB is optionally substituted with one or more substituents each of which is independently halogen, hydroxy, —$C_1$–$C_6$ haloalkyl, —O—$C_1$–$C_6$ alkyl, or —O—$C_1$–$C_6$ haloalkyl;
HetB in $R^5$ is a 5- or 6-membered monocyclic aromatic ring containing from 1 to 4 heteroatoms independently selected from N, O and S; and $R^6$ and $R^7$ are each independently —H, —$C_1$-$C_6$ alkyl, —$C_1$-$C_6$ haloalkyl, —$C_3$-$C_6$ cycloalkyl, or aryl, wherein aryl is selected from phenyl and naphthyl, and is optionally substituted with one or more substituents each of which is independently halogen, —OH, $C_1$-$C_6$ alkyl, —$C_1$-$C_6$ haloalkyl, —O—$C_1$-$C_6$ alkyl, or —O—$C_1$-$C_6$ haloalkyl; or alternatively $R^6$ and $R^7$ together with the carbons to which each is attached form a fused benzene ring which is optionally substituted with one or more substituents each of which is independently halogen, —OH, —$C_1$-$C_6$ alkyl, —$C_1$-$C_6$ haloalkyl, —O—$C_1$-$C_6$ alkyl, or —O—$C_1$-$C_6$ haloalkyl.

17. The process according to claim 16, wherein the treatment is conducted at a temperature in a range of from about −10 to about 85° C.

18. The process according to claim 16, wherein the iodine monohalide is employed in an amount of from about 1 to about 5 equivalents per equivalent of olefin II.

19. The process according to claim 16, wherein the treatment is conducted with vigorous agitation.

20. The process according to claim 16, wherein the pH is controlled by on-demand addition of base.

21. The process according to claim 16, wherein the organic solvent is selected from the group consisting of $C_1$-$C_6$ linear and branched halogenated alkanes, dialkyl ethers wherein each alkyl is independently a $C_1$-$C_4$ alkyl, $C_1$-$C_6$ linear and branched alkanes substituted with two —O—$C_1$-$C_4$ alkyl groups (which are the same or different), $C_4$-$C_6$ cyclic ethers and diethers, $C_1$-$C_4$ alkyl esters of $C_1$-$C_6$ alkylcarboxylic acids, and $C_2$-$C_4$ aliphatic nitriles.

22. The process according to claim 16, wherein the olefin is:

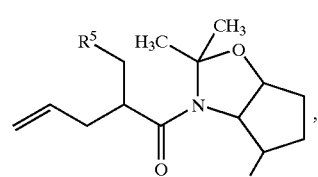
(III)

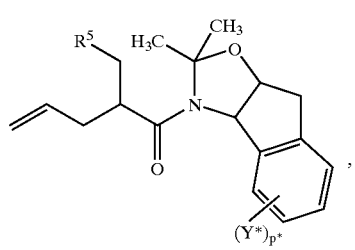
(IV)

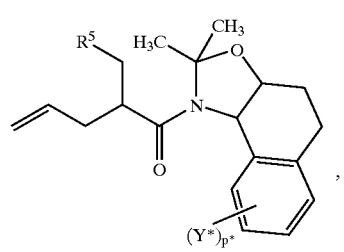
(V)

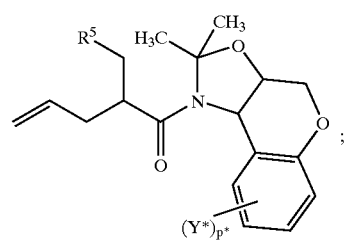
(VI)

wherein:

$R^5$ is $C_1$-$C_6$ alkyl, $C_3$-$C_6$ cycloalkyl, phenyl, naphthyl, or HetB; wherein the alkyl, cycloalkyl, phenyl, naphthyl, or HetB is optionally substituted with one or more substituents each of which is independently halogen, hydroxy, —$C_1$-$C_6$ haloalkyl, —O—$C_1$-$C_6$ alkyl, or —O—$C_1$-$C_6$ haloalkyl;

HetB in $R^5$ is a 5- or 6-membered monocyclic aromatic ring containing from 1 to 4 heteroatoms independently selected from N, O and S; and $R^6$ is —H, —$C_1$-$C_6$ alkyl, —$C_1$-$C_6$ haloalkyl, —$C_3$-$C_6$ cycloalkyl, or phenyl, wherein the phenyl is optionally substituted with one or more substituents each of which is independently halogen, —OH, —$C_1$-$C_6$ alkyl, —$C_1$-$C_6$ haloalkyl, —O—$C_1$-$C_6$ alkyl, or —O—$C_1$-$C_6$ haloalkyl;

each Y* is independently —H, halogen, —$C_1$-$C_4$ alkyl, —$C_1$-$C_4$ fluoroalkyl, or —O—$C_1$-$C_4$ alkyl; and p* is an integer equal to zero, 1 or 2.

23. The process according to claim 22, wherein:

the treatment is conducted at a temperature in a range of from about −10 to about 85° C.;

the iodine monohalide is iodine monochloride employed in an amount of from about 1 to about 5 equivalents per equivalent of the olefin;

the treatment is conducted with vigorous agitation; and the solvent is selected from the group consisting of $C_1$-$C_6$ linear and branched halogenated alkanes, dialkyl ethers wherein each alkyl is independently a $C_1$-$C_4$ alkyl, $C_1$-$C_6$ linear and branched alkanes substituted with two —O—$C_1$-$C_4$ alkyl groups (which are the same or different), $C_4$-$C_6$ cyclic ethers and diethers, $C_1$-$C_4$ alkyl esters of $C_1$-$C_6$ alkylcarboxylic acids, and $C_2$-$C_4$ aliphatic nitriles.

24. The process according to claim 23, wherein the olefin is

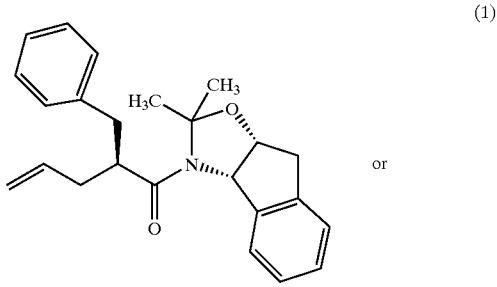
(1)

or

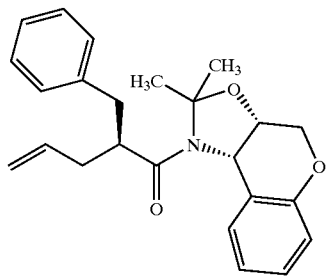
; and the iodohydrin is
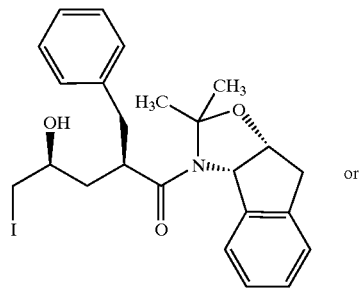
or
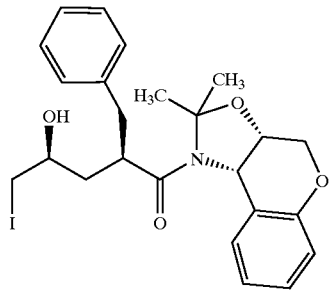
25. The process according to claim 24, wherein:
the treatment is conducted at a pH of from about 7 to about 10;
the treatment is conducted at a temperature in a range of from about 10 to about 50° C.;
the iodine monochloride is employed in an amount of from about 1 to about 1.8 equivalents per equivalent of the olefin; and
the solvent is a $C_1$–$C_4$ alkyl acetate.
* * * * *